United States Patent [19]

Czernichow

[11] Patent Number: 4,757,709
[45] Date of Patent: Jul. 19, 1988

[54] FLOWMETER FOR USE IN A HYDROCARBON WELL

[75] Inventor: Jean A. Czernichow, Chatenay, France

[73] Assignee: Schlumberger Technology Corporation, Houston, Tex.

[21] Appl. No.: 17,379

[22] Filed: Feb. 20, 1987

[51] Int. Cl.$^4$ .............................................. E21B 47/10
[52] U.S. Cl. ................... 73/155; 73/861.65
[58] Field of Search ................ 73/155, 861.65, 861.67; 166/250

[56] References Cited

U.S. PATENT DOCUMENTS 2,377,501  6/1945  Kinley .......................... 73/155 UX
3,357,492  12/1967  Hubby ............................ 73/155 X Primary Examiner—Jerry W. Myracle
Attorney, Agent, or Firm—Henry N. Garrana

[57] ABSTRACT

The flowmeter comprises a central mandrel suspended from a cable and centered in the fluid stream so as to leave an annular passage. Fluid stream contracting means are provided for forming a venturi in the annular passage, and a differential pressure gauge is provided in the central mandrel to produce a signal representative of the pressure head loss across the venturi, which signal is processed to derive the flow rate.

7 Claims, 3 Drawing Sheets

FLOWMETER FOR USE IN A HYDROCARBON WELL

The present invention relates to a device for measuring the flow rate of a fluid flowing in a vertical stream, and in particular a fluid flowing up a hydrocarbon well.

FIELD OF THE INVENTION

More specifically, the invention relates to a flowmeter of the type comprising: a hollow central mandrel suspended from a cable and provided with means for centering it in the stream while leaving an annular fluid flow passage; measuring means housed at least in part in the mandrel and intended to provide signals representative of the fluid flow rate in the stream; and an electronic assembly for receiving and processing said signals.

BACKGROUND OF THE INVENTION

Devices of the above-specified type are described, in particular, in U.S. Pat. Nos. 3,630,078 and 3,934,467. Both of these documents describe helical rotor flowmeters, in which the measuring means are constituted by a spinner immersed in the fluid stream and rotating at a rate which is a function of the flow rate. A drawback associated with such devices is that they include a large number of mechanical moving parts which are fragile and difficult to construct. Another drawback is that the space occupied by the spinner makes it difficult to insert in a fluid stream, particularly when the spinner must be passed through zones of small cross section: proposals have even been made for spinners having retractable blades, thereby further complicating the flowmeter as a whole. Finally, whenever a spinner is inserted in a stream, an obstruction is set up and under some circumstances this may be undesirable.

The aim of the present invention is to provide a nonintrusive flowmeter, and in particular a flowmeter which does not include a spinner, but which is simple in structure and which includes a minimum of moving parts.

SUMMARY OF THE INVENTION

The present invention achieves this aim by providing a flowmeter comprising:

a central mandrel adapted to be suspended from a cable in a well;

means for centering the mandrel in the fluid steam to define an annular flow passage;

fluid stream restricting means for creating a restriction in said annular flow passage;

a differential pressure gauge located in the mandrel and responsive to the pressure head loss resulting from said restriction, for generating a signal indicative of the flow rate of the fluid stream.

Such a flowmeter is particularly suitable for measuring a flow rate in a production string of a hydrocarbon well, in which case it is advantageous for the mandrel to include a device for fixing it to the downhole valve in such a production string.

A device may be provided for measuring fluid density, in which case it is preferably constituted by a second differential pressure gauge having pressure measuring take-off points situated on the central mandrel, and may be constituted by a device of the type described in U.S. Pat. No. 3,455,157.

The cable from which the flowmeter is suspended preferably includes at least one electrical conductor for transmitting signals to a processing apparatus situated on the surface, as described, for example, in U.S. Pat. No. 3,934,467. However, it is advantageous for the hollow mandrel itself to house all, or at least a portion, of the electronic signal-processing equipment.

The stream-restricting means may be constituted by a local radial expansion in the wall delimiting the outside of the stream, and in particular in the wall of the production string.

Alternatively, or in association with the above-described disposition, the stream-restricting means may be constituted by a local outward radial expansion of the mandrel.

These local expansions may be permanent or temporary. In particular, the local expansion of the mandrel may be obtained by one or more removable matching sleeves suitable for optimizing the flow passage as a function of the flow rates to be measured.

A flowmeter in accordance with the invention is easy to install and provides rapid measurements of flow rates of different fluid phases in a well. Once the measurements have been performed, the flowmeter may be withdrawn from the well.

Naturally, a flowmeter in accordance with the invention can be used equally well to determine a volume flow rate or a mass or weight flow rate.

BRIEF DESCRIPTION OF THE DRAWINGS

An embodiment of the invention is described by way of example with reference to the accompanying drawings, in which.

MORE DETAILED DESCRIPTION

Figure 1:
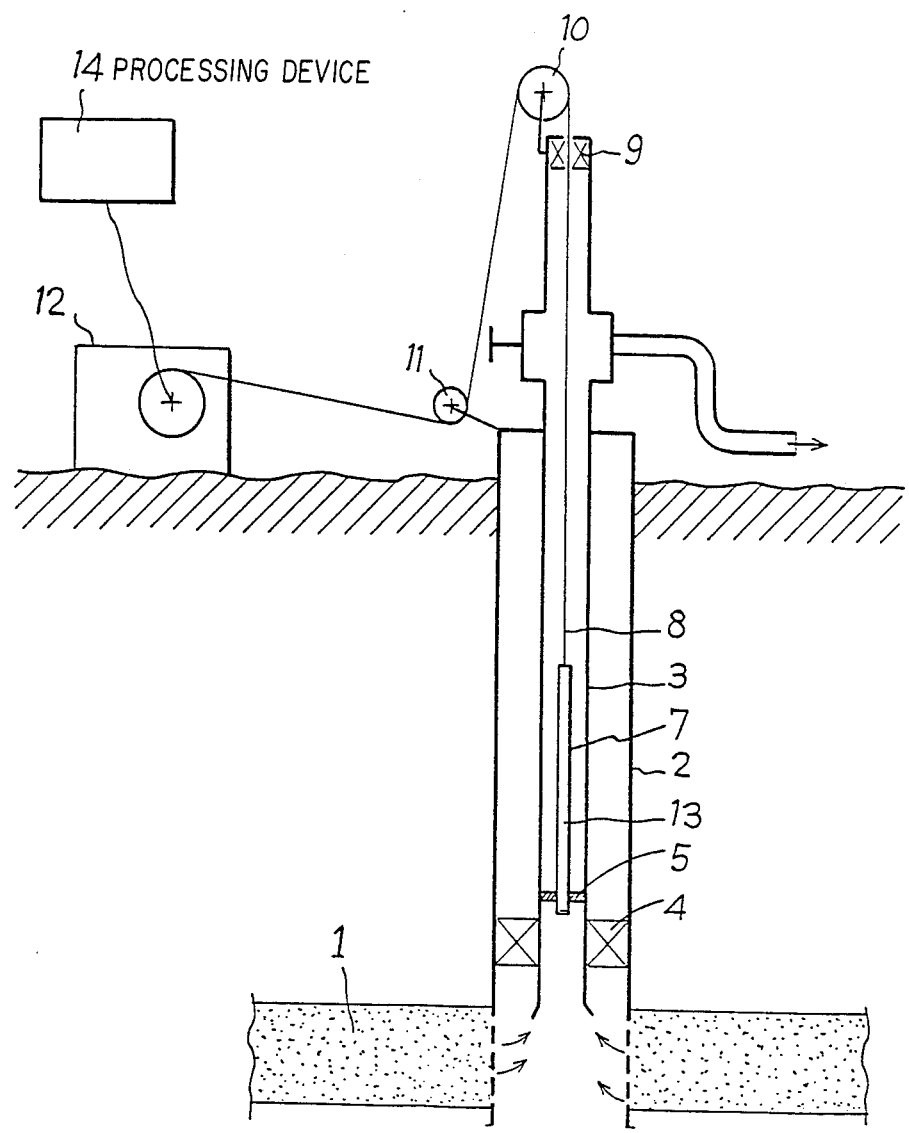
FIG. 1 is a general diagram showing the best position for locating the flowmeter mandrel in a hydrocarbon well.

FIG. 1 shows a well passing through an oil-producing zone 1 and comprising a production string 3 located within a casing 2. An annular sealing device 4 is located between the bottom end of the casing 2 and the production string 3.

A downhole valve is shown symbolically at 5 and enables the production string 3 to be closed off at will at its bottom end by means not shown. By way of example, this downhole valve may be a valve of the type described in the European patent application published under the U.S. Pat. No. 0,134,734 and filed July 12, 1984. A central mandrel 7 is suspended from a cable 8 which emerges from the top of the production string via a sealing device 9 and then passes via pulleys 10 and 11 prior to being wound onto the drum of a winch 12 disposed on the surface of the ground.

The central mandrel 7 is hollow and houses the measurement devices and electronic equipment associated therewith. In particular, the bottom section 13 of the mandrel located above the downhole valve 5 is suitable for housing a pressure gauge which is exposed to the pressure existing in the well below the valve via channels passing through the mandrel.

The cable 8 is an electrical cable which, in addition to its mechanical function of suspending and actuating the mandrel, also conveys measurement signals to the surface, e.g. the signals generated by the pressure gauge housed in said section 13. These signals may be completely or partially processed and/or stored by the electronic equipment housed in the mandrel 7, and on reaching the surface they are processed, stored, or displayed by means of a device 14.

The above-described dispositions are well known to the person skilled in the art and a more detailed description is unnecessary.

Figure 2:
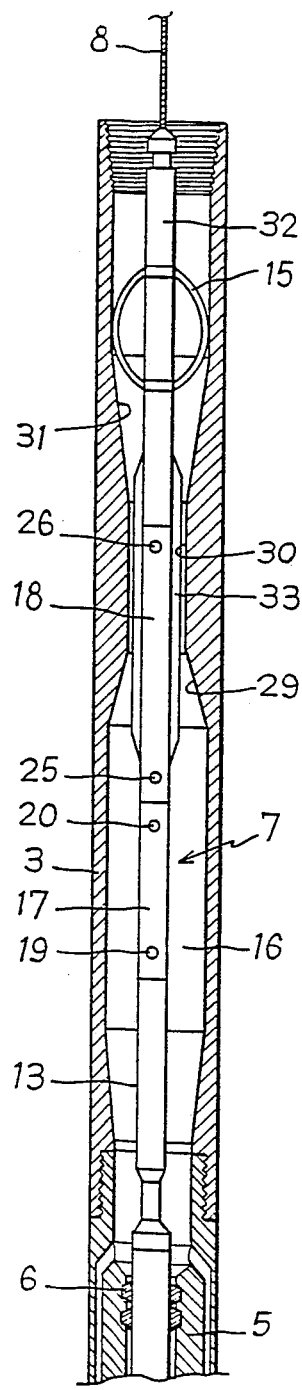
FIG. 2 is a longitudinal section through a production string and showing a flowmeter in accordance with the invention.
Figure 3:
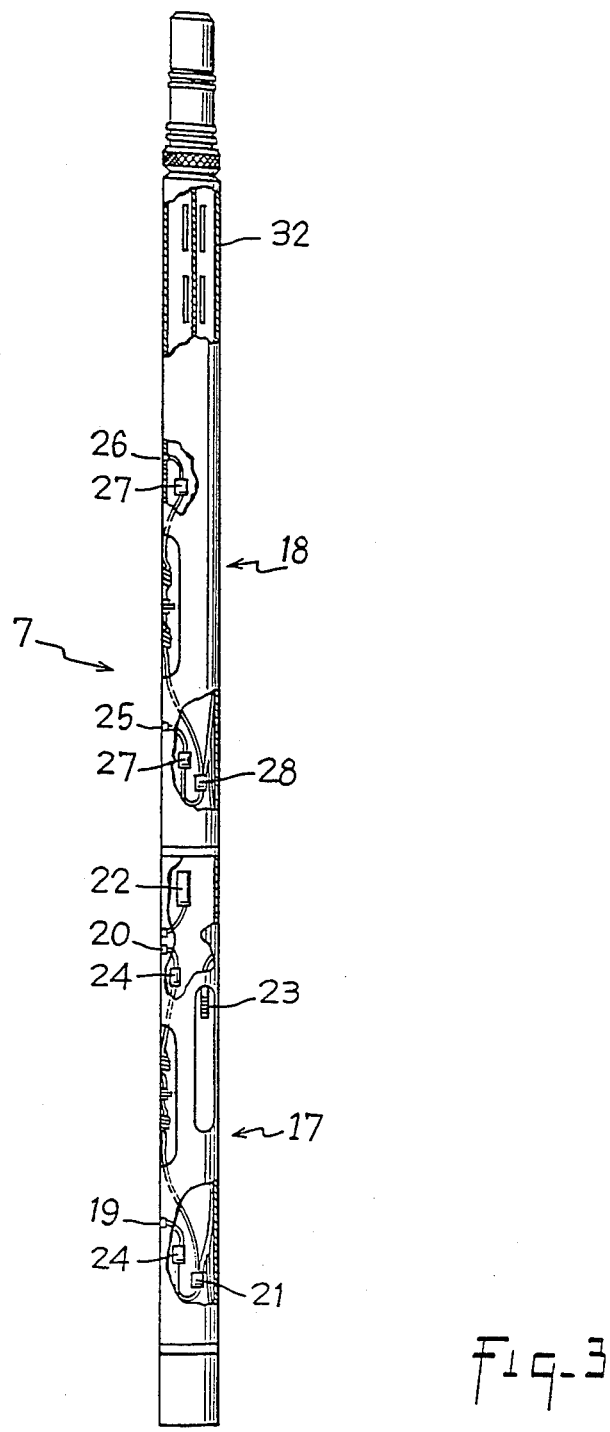
FIG. 3 is a partially cut away side view of the flowmeter showing its main internal members.

Reference is now made to FIGS. 2 and 3. The mandrel 7 is fixed to the downhole valve 5 by locking means 6 and is centered by one or more centralizers 15. An annular passage 16 is reserved for the fluid flow between the mandrel 7 and the production string 3.

The mandrel 7 includes two measurement stages 17 and 18.

The stage 17 houses a differential pressure gauge which may advantageously be the type described in U.S. Pat. No. 3,455,157, which is incorporated in the present application by reference. This differential pressure gauge includes two measurement points 19 and 20 which are separated in the direction of fluid displacement along the annular flow, with the cross-section thereof being constant in this portion. Filters 24 are provided in order to protect the measuring apparatus upstream from said measurement points. The pressure differential is essentially a function of the density of the fluid. The electrical signal provided by a differential pressure sensor 21 is representative, in correlation with signals from a temperature sensor 23 and an absolute pressure sensor 22 of the density of the fluid flowing along the annular stream.

The stage 18 also houses a differential pressure gauge which may be entirely similar to the differential pressure gauge of the stage 17, and which thus comprises two measurement points 25 and 26 which are longitudinally separated from each other, together with their protective filters 27 and a differential pressure sensor 28. However, unlike the stage 17 which is situated in a region of the fluid stream which is of constant cross-section, the stage 18 is situated in a region where the flow cross-section restricts in order to form an annular venturi. This restriction in section is obtained by means of an upwardly tapering portion 29 of the inside wall of the production string 3, followed by a throat 30 of constant cross-sectional area, and then followed by a flared portion 31. The upstream measuring point 25 is situated in the region of non-reduced cross-section, while the downstream measurement point 26 is situated in a region of reduced cross-section, level with the throat of the venturi. In a manner conventional for nozzle flowmeters, the mass flow rate (after appropriate corrections) is proportional to the square root of the product of the density of the fluid multiplied by the pressure difference between the measurement points. Since the density of the fluid can be determined from the signals generated by the differential pressure gauge of the stage 17, the measurement by the stage 18 of the pressure difference between the upstream end and the throat of the venturi can be used to determine the fluid flow rate up the production string. This determination may be performed by electronic equipment integrated in the mandrel 7 and housed, for example, in the top section 32 thereof, or alternatively by surface equipment 14.

The restriction in the section is determined so as to optimize measurement as a function of the expected flow rates. In order to adapt the apparatus to several different flow rates, a removable sleeve 33 may be provided around the mandrel 7 at the venturi, thereby further reducing the area of the flow passage at the throat of the venturi. This sleeve has an orifice compatible with the measuring point 26.

In a particular embodiment, the production string 3 has an inside diameter of 107 mm around the stage 17, and the mandrel 7 has an outside diameter of 43 mm, thereby leaving a flow passage of 75.4 cm$^2$. The throat of the venturi has an inside diameter of 71 mm, thus leaving a reduced section of 25 cm$^2$. The ratio between the upstream section and the reduced section is thus 3:1, which is advantageous for measuring average to high flow rates. The adaptor sleeve 33 has an outside diameter of 51 mm, leaving a reduced section of 19 cm$^2$, thus changing the area ratio to about 4:1, which is advantageous for measuring low to average flow rates.

What I claim is:

1. A device for measuring the flow rate of a fluid stream in a hydrocarbon well, comprising:
   a central mandrel adapted to be suspended from a cable in the well,
   means for centering the mandrel in the fluid stream to define an annular flow passage,
   fluid stream contracting means for creating a restriction in said annular flow passage,
   a differential pressure gauge located in the mandrel and responsive to the pressure head loss resulting from said restriction, for generating a signal indicative of the flow rate of the fluid stream.

2. The device according to claim 1, wherein the fluid flows inside a production tubing provided in the well and said fluid stream contracting means comprises an internal radial expansion of the production tubing.

3. The device of claim 2, wherein a downhole valve is provided at the bottom of the production tubing and the mandrel comprises means for securing said mandrel to the downhole valve.

4. The device according to claims 1 and 2, wherein said fluid stream contracting means comprises a sleeve mounted around the mandrel.

5. The device of claim 4, wherein the sleeve has an outside diameter defined as a function of the expected range of flow rates.

6. The device of claim 1, further comprising sensor means in said mandrel for generating a signal indicative of the density of the fluid in the stream.

7. The device of claim 6, wherein said sensor means is a differential pressure gauge having pressure take-off points in a portion of the fluid stream of constant cross-section.

* * * * *